(12) United States Patent
Jahns et al.

(10) Patent No.: US 8,841,223 B2
(45) Date of Patent: Sep. 23, 2014

(54) DENTAL CERAMIC ARTICLE, PROCESS FOR PRODUCTION AND USE THEREOF

(75) Inventors: Michael Jahns, Gilching (DE); Gallus Schechner, Seefeld (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/131,428

(22) PCT Filed: Oct. 26, 2009

(86) PCT No.: PCT/US2009/062029
§ 371 (c)(1),
(2), (4) Date: May 26, 2011

(87) PCT Pub. No.: WO2010/062541
PCT Pub. Date: Jun. 3, 2010

(65) Prior Publication Data
US 2011/0236860 A1  Sep. 29, 2011

(30) Foreign Application Priority Data

Nov. 27, 2008  (EP) .................................. 08170071

(51) Int. Cl.
*C04B 35/48* (2006.01)
*C04B 35/49* (2006.01)
*C09K 3/00* (2006.01)
*A61K 6/00* (2006.01)
*A61K 6/02* (2006.01)
*C04B 35/486* (2006.01)
*A61C 13/00* (2006.01)

(52) U.S. Cl.
CPC ......... *A61K 6/0094* (2013.01); *C04B 2235/661* (2013.01); *C04B 2235/604* (2013.01); *C04B 2235/612* (2013.01); *C04B 2235/616* (2013.01); *C04B 2235/72* (2013.01); *A61K 6/025* (2013.01); *C04B 2235/602* (2013.01); *A61K 6/024* (2013.01); *C04B 2235/77* (2013.01); *C04B 2235/449* (2013.01); *C04B 2235/96* (2013.01); *A61K 6/0005* (2013.01); *C04B 2235/3224* (2013.01); *C04B 2235/9661* (2013.01); *C04B 2235/3225* (2013.01); *C04B 35/486* (2013.01); *A61C 13/00* (2013.01); *C04B 2235/6027* (2013.01); *A61K 6/0255* (2013.01)
USPC .............................. 501/103; 501/104; 106/35

(58) Field of Classification Search
USPC .................. 501/103, 104; 106/35; 433/201.1, 433/202.1, 203.1
See application file for complete search history.

(56) References Cited

U.S. PATENT DOCUMENTS

| | | | |
|---|---|---|---|
| 3,957,500 A * | 5/1976 | Pitts .............................. | 501/103 |
| 4,758,541 A | 7/1988 | Tsukuma | |
| 5,263,858 A | 11/1993 | Yoshida et al. | |
| 6,576,354 B2 * | 6/2003 | Tsukatani et al. ............ | 428/702 |
| 6,709,694 B1 | 3/2004 | Suttor et al. | |
| 6,713,421 B1 | 3/2004 | Hauptmann et al. | |
| 6,769,912 B2 | 8/2004 | Beuschel et al. | |
| 2003/0132539 A1 | 7/2003 | Althoff et al. | |
| 2004/0119180 A1 * | 6/2004 | Frank et al. ..................... | 264/16 |
| 2005/0060948 A1 | 3/2005 | Rosenflanz | |
| 2007/0292597 A1 | 12/2007 | Ritzberger et al. | |

FOREIGN PATENT DOCUMENTS

| | | |
|---|---|---|
| EP | 0 455 854 | 11/1991 |
| EP | 1 486 476 | 12/2004 |
| EP | 1 818 318 A2 | 8/2007 |
| JP | 62 123042 | 6/1987 |
| WO | WO 00/06796 | 2/2000 |

OTHER PUBLICATIONS

Feist, J.P. et al., "Europium-doped yttria-stabilized zirconia for high-temperature phosphor thermometry", Proceedings of the Institution of Mechanical Engineers, vol. 214, Part L, (2000) p. 7-12.

García-Hipólito, M. et al., "Cathodoluminescent and photoluminescent properties of terbium doped $ZrO_2$ films prepared by pneumatic spray pyrolysis technique", Journal of Luminescence 93 (2001) p. 9-15.

Hypänen, I., et al., "Upconversion Properties of Nanycrystalline $ZrO_2$:$Yb^{3+}$, $Er^{3+}$ Phosphors" Journal of Nanomaterials, vol. 2007, Article ID 16391, 8 pages.

Rambabu, U., et al., "Fluorescence spectra of Tm$^{3+}$-doped rare earth oxychloride powder phosphors", Materials Chemistry and Physics, vol. 43 (1996), p. 195-198.

Reisfeld, R., et al., "Fluorescence study of zirconia films doped by Eu$^{3+}$, Tb$^{3+}$ and Sm$^{3+}$ and their comparison with silica films", Journal of Alloys and Compounds, vol. 300-301 (2000) p. 147-151.

PCT International Search Report for PCT/US2009/062029, dated Mar. 30, 2010, 3 pages.

* cited by examiner

Primary Examiner — Noah Wiese
(74) Attorney, Agent, or Firm — Qiang Han; 3M Innovative Properties Company

(57) ABSTRACT

The invention describes a dental article comprising zirconium oxide and at least two different coloring substances A and B, substance A showing a light emission in the range of about 470 nm to about 510 nm and substance B showing a light absorption in the range from about 520 nm to about 750 nm. The invention also relates to different processes of producing the dental article e.g. by a process comprising a casting step, a pressing step, or an infiltration step and to the use of certain compositions containing either substance A or substance B for producing such a dental article.

13 Claims, 8 Drawing Sheets

DENTAL CERAMIC ARTICLE, PROCESS FOR PRODUCTION AND USE THEREOF

CROSS REFERENCE TO RELATED APPLICATIONS

This application is a national stage filing under 35 U.S.C. 371 of PCT/US2009/062029, filed Oct. 26, 2009, which claims priority to European Patent Application No. 08170071.8, filed Nov. 27, 2008, the disclosures of which are incorporated by reference in their entirety herein.

FIELD OF THE INVENTION

The invention generally relates to a dental article comprising zirconium oxide and at least two different substances A and B, having certain light emission and light absorption properties. The dental article can be used e.g. in the field of dentistry for producing dental crowns and bridges.

BACKGROUND ART

U.S. Pat. No. 4,758,541 relates to a zirconia sintered body comprising, in addition to $ZrO_2$, $Y_2O_3$ and $TiO_2$, 0.1 to 3 mol % of an oxide of a rare earth element of the lanthanum group having a fluorescence-radiating property as well as a high translucence.

U.S. Pat. No. 6,709,694 relates to the coloring of ceramics by means of ionic or complex-containing solutions. Solutions preferred for this contain defined concentrations of at least one of the salts or complexes of the rare earth elements or the elements of the subgroups.

U.S. Pat. No. 6,713,421 relates to blanks comprising zirconium oxide-based ceramic with an addition of 0.1 to 0.50 wt.-% of at least one of the oxides of the elements aluminium, gallium, germanium, indium and their use.

US 2007/0292597 relates to compositions based on $ZrO_2$ and single- and multi-colored blanks made from oxide ceramics and a process for their preparation, in which oxide ceramic powder is coated with a colouring substance.

EP 1 818 318 A2 describes a production method of a dental ceramics material comprising the step of mixing a pink coloring agent and a yellow coloring agent at a certain mixing ratio with zirconium oxide. As the pink coloring agent manganese oxide is used and as the yellow coloring agent vanadium oxide is used. These additives absorb light.

US 2005/0060948 refers to a method of making glass-ceramics comprising $Al_2O_3$, rare earth oxides, at least one of $ZrO_2$ or $HfO_2$ and at least one of $Nb_2O_5$ or $Ta_2O_5$.

U.S. Pat. No. 5,263,858 is directed to an ivory-colored zirconia sintered body containing stabilizer-containing $ZrO_2$ as a main component and also containing certain amounts of $Er_2O_3$, $Pr_6O_{11}$, $Fe_2O_3$ and ZnO.

There is still room for improvement especially with regard to the requirements to be fulfilled with respect to modern dental materials. Many of the commercially available dental restorations still do not show the appearance of natural dental teeth.

However, patients and dentists nowadays have an increasing demand for aesthetic dentures.

Thus, it is one object of the invention to provide a dental article which can be used for making aesthetic dental restorations.

DESCRIPTION OF THE INVENTION

In one embodiment the present invention features a dental article, especially a dental ceramic article and according to a preferred embodiment a dental support structure, comprising zirconium oxide and at least two different substances A and B, substance A showing a light emission in the range of about 480 nm to about 510 nm and substance B showing a light absorption in the range of about 520 nm to about 750 nm, preferably in the range of about 550 to about 630 nm, substance A and substance B usually being materials which are different from each other.

In another embodiment, the invention relates to different processes of producing the dental article as described in the text of the invention e.g. by a process comprising a casting step, a pressing step, or an infiltration step.

Moreover, the invention features the use of the dental article as described in the text of the invention for producing of crowns, bridges and parts thereof.

The invention is also directed to the use of either a composition containing a substance A or a composition containing a substance B for producing a dental article containing zirconium oxide, wherein the dental article obtained after the production process comprises substance A and substance B and wherein substance A and substance B are as described in the text of the present invention.

A further aspect of the invention relates to a composition to be used in a process for producing a dental article, the composition comprising
  a solvent in an amount of about 20 to about 99 wt.-%,
  either substance A or substance B or substance A and substance B, and
  optionally additives in an amount of about 0.1 wt.-% to about 10 wt.-%,
wherein, if substance A is present, substance A is present in an amount of about 1 wt.-% to about 50 wt.-%, and if substance B is present, substance B is present in an amount of about 0.1 wt.-% to about 20 wt.-%, wt.-% with respect to the weight of the whole composition, and wherein substance A and substance B are as described in the text of the present invention.

Definitions

Unless otherwise specified, within the description of the present invention, the following terms have the following meaning:

The term "showing a light emission or light absorption" within a certain range means that at least one emission band or absorption band within this range can be found. This does not necessarily exclude the presence of further emission or light absorption bands outside this particular range.

The term "dental article" is to be understood as an article which can and is to be used in the dental and/or orthodontic area including dental laboratories. In view of regulatory requirements dental articles have to fulfil certain standards. A typical example of a dental article is a dental restoration.

The term "dental restoration" means any restoration which can be used in the dental field. In this respect, the dental restoration shall have sufficient strength. Dental restorations are typically comprised of at least two parts: a dental support structure and a dental veneer or facing. Examples include crowns, abutments and bridges (including 2, 3, 4, 5, 6, 7 or even 8 parts bridges).

Dental support structures are typically made of or comprise oxide ceramic materials including $ZrO_2$ or $Al_2O_3$. Compared to other framework such as pottery or paving stones, the dental support structure is small and filigree and of high strength. The thickness of the dental support structure can vary from very thin, e.g. at the edges and rims (below about 0.1 mm) to considerably thick, e.g. in the biting area (up to about 7 mm). Dental support structures do typically not comprise a glass ceramic material.

"Ceramic" means an inorganic non-metallic material that is produced by application of heat. Ceramics are usually hard, porous and brittle and, in contrast to glasses or glass ceramics, display an essentially purely crystalline structure.

"Glass-ceramic" means an inorganic non-metallic material where one or more crystalline phases are surrounded by a glassy phase.

By "dental mill blank" is meant a solid block (3-dimensional (3-dim) article) of material from which a dental article, dental workpiece, dental support structure or dental restoration can be machined. A dental mill blank may have a size of about 20 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm.

By "machining" is meant milling, grinding, cutting, carving, or shaping a material by a machine. Milling is usually faster and more cost effective than grinding.

A dental ceramic article is classified as "pre-sintered" if the dental ceramic article has been treated with heat (temperature range from about 900 to about 1100° C.) for about 1 to about 3 h to such an extend that the raw breaking resistance of the dental ceramic article is within a range of about 5 to about 55 MPa or about 5 to about 30 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 20 mm, thickness of sample disc: 2 mm; no grinding and polishing of samples.).

A pre-sintered dental ceramic article typically has a porous structure and its density (usually 3.0 $g/cm^3$ for an Yttrium stabilized $ZrO_2$ ceramic) is less compared to a completely sintered dental ceramic article (usually 6.1 $g/cm^3$ for an Yttrium stabilized $ZrO_2$ ceramic). The diameter of the pores can be in a range of about 50 nm to about 150 nm (corresponding to about 500 to about 1500 Å). A typical pore diameter is about 120 nm.

The terms "sintering" or "firing" are used interchangeably. A pre-sintered ceramic framework shrinks during a sintering step, that is, if an adequate temperature is applied. The sintering temperature to be applied depends on the ceramic material chosen. For $ZrO_2$ based ceramics a typical sintering temperature range is about 1200° C. to about 1500° C. $Al_2O_3$ based ceramics are typically sintered in a temperature range of about 1300° C. to about 1700° C. Glass ceramic materials are typically sintered in a range of about 700 to about 1100° C. for about 1 to about 3 h.

Sintering typically includes the densification of a porous material to a less porous material (or a material having less cells) having a higher density, in some cases sintering may also include changes of the material phase composition (for example, a partial conversion of an amorphous phase toward a crystalline phase).

"Density" means the ratio of mass to volume of an object. The unit of density is typically $g/cm^3$. The density of an object can be calculated e.g. by determining its volume (e.g. by calculation or applying the Archimedes principle or method) and measuring its mass.

A "green body" means an un-sintered ceramic item.

A "particle" means a substance being a solid having a shape which can be geometrically determined. The shape can be regular or irregular. Particles can typically be analysed with respect to e.g. grain size and grain size distribution.

A "powder" means a dry, bulk solid composed of a large number of very fine particles that may flow freely when shaken or tilted.

"Casting" means a manufacturing process by which a liquid material (e.g. solution or dispersion) is poured into a mould, which contains a hollow cavity of the desired shape, and then allowed to solidify.

A "liquid" within the meaning of the invention is any solvent or liquid which is able to at least partially disperse or dissolve the inorganic binder at ambient conditions (e.g. 23° C.).

"Ambient conditions" invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

A composition or solution is "essentially or substantially free of" a certain component within the meaning of the invention, if the composition or solution does not contain said component as an essential feature. Thus, said component is not willfully added to the composition or solution either as such or in combination with other components or ingredient of other components. Ideally the composition or solution does not contain the said component at all. However, sometimes the presence of a small amount of the said component (e.g. up to about 0.1 or up to about 0.01 or up to about 0.001 wt.-% with respect to the weight of the dental article) is not avoidable e.g. due to impurities contained in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

BRIEF DESCRIPTION OF FIGURES

FIG. 1 *b* shows a flow chart of possible production route comprising a pressing step.

FIG. 1 *c* shows a flow chart of possible production route comprising a pressing and infiltration step.

FIG. 2 *b* shows the fluorescence spectrum of a sample containing no colouring additives.

FIG. 2 *c* shows the fluorescence spectrum of a sample containing dysprosium oxide.

FIG. 2 *d* shows the fluorescence spectrum of a sample containing erbium carbonate.

FIG. 2 *e* shows the fluorescence spectrum of a sample containing europium oxide.

FIG. 2 *f* shows the fluorescence spectrum of a sample containing dysprosium oxide, erbium carbonate and europium oxide.

DETAILED DESCRIPTION OF THE INVENTION

Figure 1A:
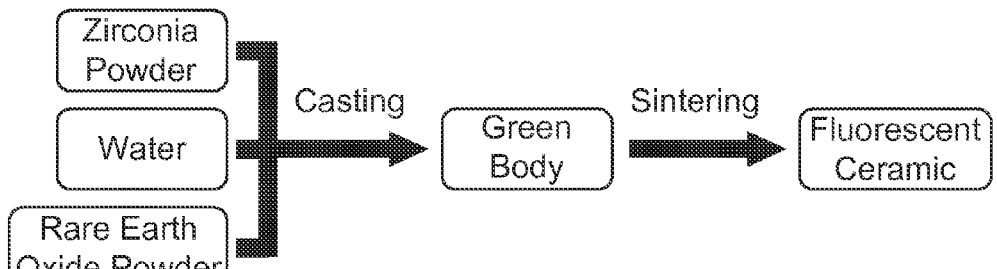
FIG. 1 *a* shows a flow chart of possible production route comprising a casting step.

It has been found that the dental article described in the text of the invention fulfils the practitioners' needs especially with regard to aesthetic properties.

The natural fluorescence inherent to human dentin is a property that ceramic restorations based on zirconium oxide were not able to match until now. Instead, fluorescence, if at all, was provided by coating glassy veneer compositions containing fluorescent components on the surface of zirconium oxide based support structures. However, this approach does not produce restorations that "shine from within".

In contrast to this former approach, the inventive dental article, which can be used as support structure in the production process of dental restorations, has fluorescent properties itself.

Fluorescent zirconium oxide containing material does not only match the behaviour of natural dentin in a dark environment with UV light present. It also facilitates the provision of dental restorations with a more natural, shining look in broad daylight. The desired natural looking or "shine" is produced inside the dental restoration through fluorescence of the zirconium oxide material used.

Some substances or additives providing fluorescent properties to dental articles sometimes show light emission in ranges of the spectrum, which may be contra-productive to the desired fluorescence properties. E.g., dysprosium shows fluorescence in a desired range of the spectrum, however, also has emission properties in a range of the visible spectrum resulting overall in a yellow coloured appearance of a sample and overlaying the more desired fluorescence.

It was found that by using or adding a further substance which shows light absorption in the range of the spectrum, which is not desirable, the non desired colour is weakened at least to some extent, having the result that the more favoured colour appearance is dominating.

Thus, by combining two different colouring substances with different light emission and/or light absorbing features, a dental article can be provided having the appearance of natural dentin material.

In Table 1, the light emission and light absorption bands of different additives (ion(s)) in a zirconia material are given. According to the present invention, an emission of blue light in the range between about 450 nm and 510 nm is typically desired.

TABLE 1

| Ion(s) | Emission band(s) (nm) | Absorption bands (nm) | | Comment |
|---|---|---|---|---|
| Dy | (1) 470-510<br>(2) 560-620<br>(3) 660-700<br>(4) 760-780 | (1) 730-760<br>(2) 780-820<br>(n.v) | according to the invention | Emission bands (3) and (4) are weak compared to (1) and (2)<br>Absorption band (1) is weak compared to (2) |
| Nd | no emission | (1) 500-550<br>(2) 560-620<br>(3) 660-700<br>(4) 720-770<br>(5) 780-830<br>(n.v.) | according to the invention | Absorption bands (1) and (3) are weak compared to (2), (4) and (5) |
| Dy + Nd | (1) 470-510<br>(2) 560-620<br>(3) 660-700<br>(4) 760-780 | (1) 500-550<br>(2) 560-620<br>(3) 660-700<br>(4) 720-770<br>(5) 780-830<br>(n.v.) | according to the invention | Major emission band of Dy and major absorption band of Nd overlap (2). Both bands weaken each other. Desired emission of blue light is pronounced (1). |
| Mn | no emission | (1) 380-700 | described in EP 1 818 318 | Very broad absorption band |
| V | no emission | (1) 380-600 | described in EP 1 818 318 | Very broad absorption band |
| Mn + V | no emission | (1) 380-700 | described in EP 1 818 318 | Very broad absorption band |
| Er | 530-590 | (1) 470-570<br>(2) 610-690<br>(3) 750-830<br>(n.v.) | described in U.S. Pat. No. 5263858 | Light emission produces a green color impression, which is not desired. |
| Pr | no emission | (1) 380-630 | described in U.S. Pat. No. 5,263,858 | Very broad absorption band |
| Fe | no emission | (1) 380-700 | described in U.S. Pat. No. 5,263,858 | Very broad absorption band |
| Zn | no emission | no absorption | described in U.S. Pat. No. 5,263,858 | Sample appears white |

TABLE 1-continued

| Ion(s) | Emission band(s) (nm) | Absorption bands (nm) | | Comment |
|---|---|---|---|---|
| Er + Pr + Fe + Zn | no emission | (1) 380-630 (2) 640-660 (3) 770-800 (n.v.) | described in U.S. Pat. No. 5,263,858 | Very broad absorption band + sharp bands from Er | n.v.: "not visible", band is outside of the visible spectrum
Multiple bands with peaks at similar wavelengths are indicated as one broad band.
Emission measurements were performed for wavelengths between 450 and 780 nm.
Absorption measurements were performed for wavelengths between 380 and 900 nm.

As can be taken from Table 1, the ions described and used in a couple of background art references do not show the desired absorption or emission bands of the inventive dental article. Especially with respect to the ions suggested e.g. in EP 1 818 318 A2, which are Mn and V, it was found that those ions do not have the desired emission in the range of 470 nm and 510 nm.

The dental article typically contains zirconium oxide in an amount of at least about 70 mol-% or at least about 80 mol-% or at least about 90 mol-% with respect to the whole composition.

The dental article can contain zirconium oxide in an amount up to about 99 mol-% or up to about 98 mol-% or up to about 97 mol-% with respect to the whole composition.

Useful ranges for zirconium oxide contained in the dental article include from about 70 to about 99 mol-% or from about 80 to about 98 mol-% or from about 90 to about 97 mol-%.

Components containing zirconium oxide are commercially available from e.g. Tosoh Corp., Japan, Toray, Japan or Internet Corp., USA.

Yttrium stabilized zirconium oxide has been proven to be advantageous, due to its stability regarding the phase transformation from tetragonal to monoclinic, rendering the material tetragonal at ambient conditions.

Besides zirconium oxide in the tetragonal phase, zirconium oxide in the cubic phase can also be used. The latter one might be preferred, if a more translucent dental article is desired.

Besides zirconium oxide, the dental article can comprise further oxides including hafnium oxide, alumina, lanthanum oxide and/or cerium oxide, if desired.

Zirconium oxide containing materials which can be used are described also in U.S. Pat. No. 6,713,421 and US 2004/0119180, the contents of which with respect to the description of zirconium oxide containing materials are herewith incorporated by reference.

Substance A contained in the dental article shows light emission (especially fluorescence emission) in the range of about 470 nm to about 510 nm or from about 430 nm to about 520 nm (determined according to the description in the measurement section below).

The dental article can contain substance A in an amount of at least about 0.1 mol-% or at least about 0.2 mol-% or at least about 0.5 mol-% with respect to the whole composition (calculation based on the ion of the element used).

The dental article can contain substance A in an amount up to about 5 mol-% or up to about 3 mol-% or up to about 2 mol-% with respect to the whole composition (calculation based on the ion of the element used).

Useful ranges for substance A contained in the dental article include from about 0.1 to about 5 mol-% or from about 0.2 to about 3 mol-% or from about 0.5 to about 2 mol-% with respect to the whole composition (calculation based on the ion of the element used).

Alternatively or in addition the amount of substance A can also be given in wt.-% based on the oxide (in this case, substance A having an oxidation number of III).

Thus, the dental article can contain substance A in an amount of at least about 0.15 wt.-% or at least about 0.3 wt.-% or at least about 0.75 wt.-% with respect to the whole composition.

The dental article can contain substance A in an amount up to about 7.5 wt.-% or up to about 4.5 wt.-% or up to about 3 wt.-% with respect to the whole composition.

Useful ranges for substance A contained in the dental article include from about 0.15 wt.-% to about 7.5 wt.-% or from about 0.3 wt.-% to about 4.5 wt.-% or from about 0.75 wt.-% to about 3 wt.-% with respect to the whole composition.

If the concentration is outside the above mentioned ranges, the desired colour appearance or light emission intensity sometimes cannot be achieved or the mechanical properties of the material may change significantly. In particular, if the concentration is above a value of about 5 mol-%, then quenching, i.e. a decrease in fluorescence can occur. Additionally, higher amounts of cubic zirconia may appear in the material due to a possible stabilization of this phase by the additive. On the other hand, if the concentration is below a value of about 0.1 mol-%, then fluorescence might be too weak to produce a visible effect.

Useful substances A include compositions or components comprising dysprosium (Dy).

Components containing dysprosium are commercially available from e.g. Aldrich, USA or Fluka, Germany.

Dysprosium containing components can be provided as oxides or water soluble compositions including acetate, citrate, carbonate, chloride and nitrate.

The use of salts or oxides of dysprosium which do not produce corrosive side products upon heating are preferred. Preferred salts include dysprosium acetate and carbonate.

According to one embodiment of the invention, substance A is contained in the dental support structure of the dental article.

Substance B contained in the dental article shows light absorption at wavelengths where substance A may show undesired light emission. Substance B is different from substance A. If substance A is dysprosium, light absorption of substance B should be in the range from about 520 nm to about 750 nm or from about 550 nm to about 650 nm (determined according to the description in the measurement section below).

The dental article can contain substance B in an amount of at least about 0.01 mol-% or at least about 0.05 mol-% or at least about 0.1 mol-% with respect to the whole composition (calculation based on the ion of the element used).

The dental article can contain substance B in an amount up to about 1 mol-% or up to about 0.5 mol-% or up to about 0.3 mol-% with respect to the whole composition (calculation based on the ion of the element used).

Useful ranges for substance B contained in the dental article include from about 0.01 to about 1 mol-% or from about 0.05 to about 0.5 mol-% or from about 0.1 to about 0.3 mol-% with respect to the whole composition (calculation based on the ion of the element used).

Alternatively or in addition the amount of substance B can also be given in wt.-% based on the oxide (in this case, substance B having an oxidation number of III).

Thus, the dental article can contain substance B in an amount of at least about 0.014 wt.-% or at least about 0.07 wt.-% or at least about 0.14 wt.-% with respect to the whole composition.

The dental article can contain substance B in an amount up to about 1.4 wt.-% or up to about 0.7 wt.-% or up to about 0.4 wt.-% with respect to the whole composition.

Useful ranges for substance B contained in the dental article include from about 0.014 wt.-% to about 1.4 wt.-% or from about 0.07 wt.-% to about 0.7 wt.-% or from about 0.14 wt.-% to about 0.4 wt.-% with respect to the whole composition.

If the concentration is outside the above mentioned ranges, the desired colour appearance sometimes cannot be achieved. In particular, if the concentration is above a value of about 1 mol-% (this value, however, may also depend on the amount of substance A in the material), then ambient light might be adsorbed in addition to the irradiated light from substance A, which may lead to a discoloration of the material. On the other hand, if the concentration is below a value of about 0.01 mol-%, then light absorption might be insufficient to remove the undesired emission band from substance A.

Useful substances B include compositions or components comprising neodymium (Nd), especially if substance A is dysprosium (Dy).

Components containing neodymium are commercially available from e.g. Aldrich, USA, Merck or Fluka, Germany.

Neodymium containing components can be provided as oxides or water soluble compositions including acetate, citrate, carbonate, chloride and nitrate.

The use of salts or oxides of neodymium or copper which do not produce corrosive side products upon heating are preferred. Preferred salts include neodymium acetate and carbonate.

Figure 5A:
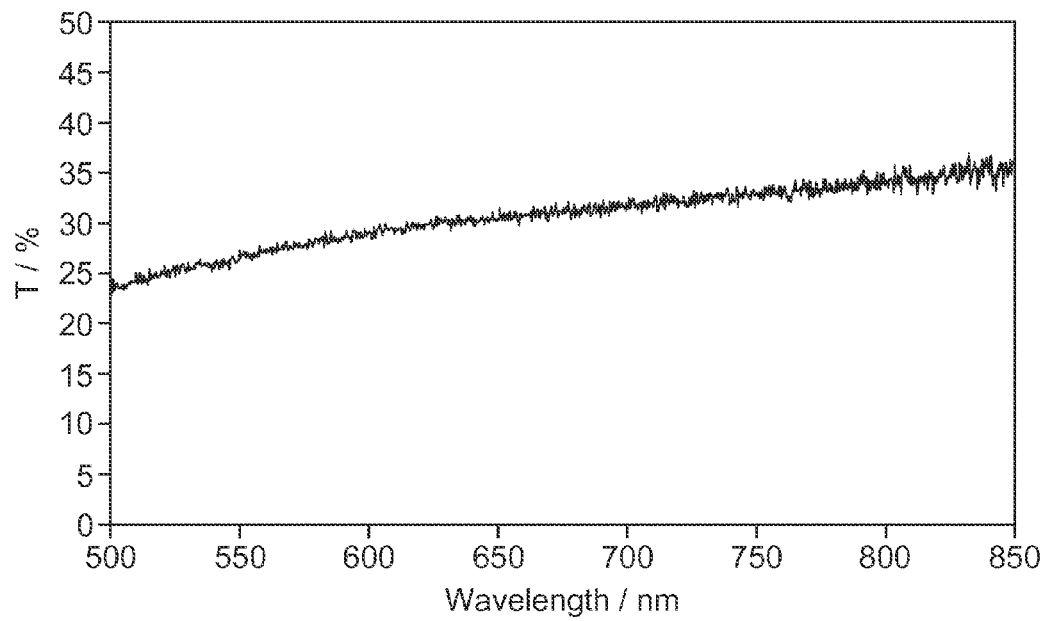
FIG. 5a shows the light transmission spectrum of 3Y-TZP zirconia without additive.
Figure 5B:
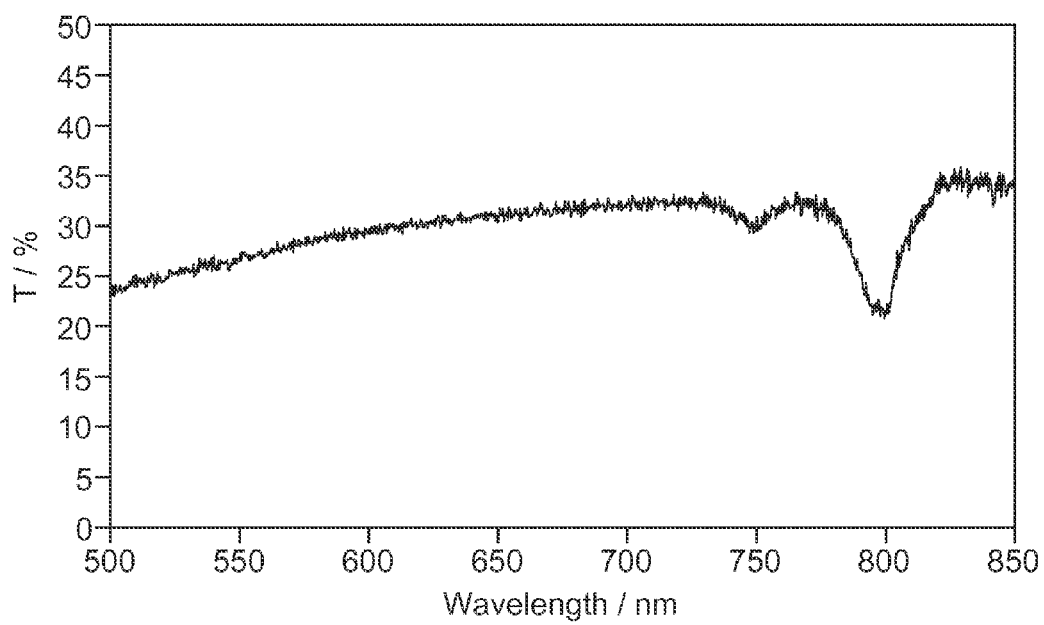
FIG. 5b shows the light transmission spectrum of 3Y-TZP zirconia with dysprosium.
Figure 5C:
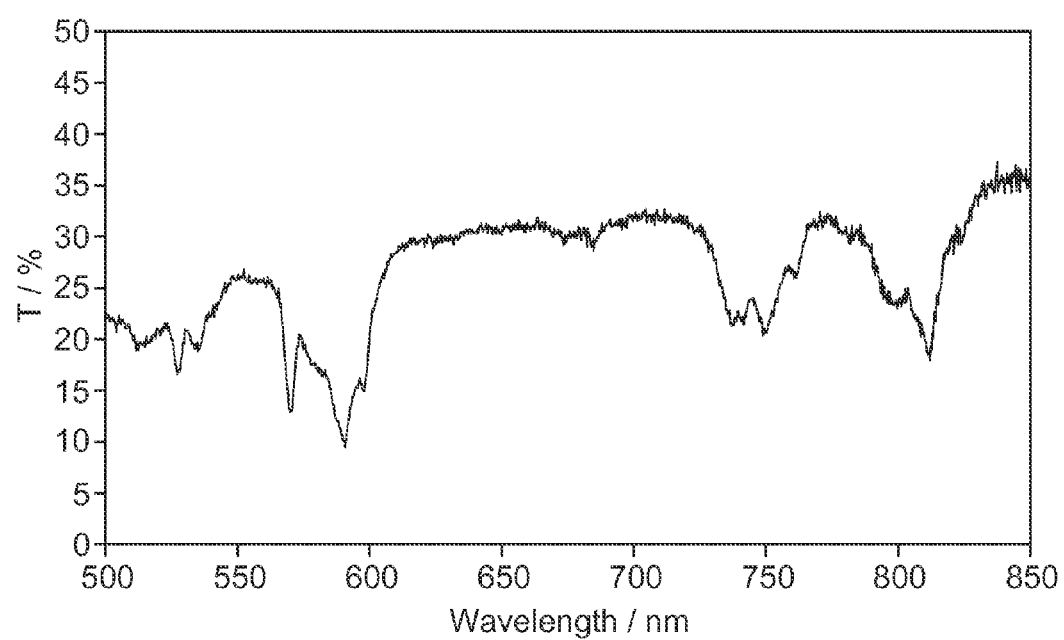
FIG. 5c shows the light transmission spectrum of 3Y-TZP zirconia with neodymium.

The respective light transmission spectrum for Nd is shown in FIG. 5c.

Substance B can be contained in the dental support structure of a dental restoration together with substance A, however, substance B can also be contained in a layer or coating typically applied directly on the dental support structure (e.g. as a liner).

Typically, substance A is used in excess relative to substance B (with respect to the molar ratio). Otherwise, the light absorption of substance B might exceed the light emission of substance A. This might lead to unwanted coloration.

A molar ratio of substance A to substance B from about 1:1 to about 500:1 or about 2:1 to about 10:1 was found to be useful (molar ratio calculated based on the ions of the respective elements).

Besides dysprosium, the dental article can contain further additives, including further colouring additives.

Further additives which can be present include erbium (Er), iron (Fe), praseodymium (Pr), manganese (Mn) and combinations thereof.

There is no need for additives to be present at all, however, it they are present they are typically present in an amount of up to about 1 wt.-% or up to about 0.1 wt.-% or up to about 0.01 wt.-% (calculation based on the ion of the element used).

Typical ranges include from about 0.0001 wt.-% to about 1 wt.-% or from about 0.001 wt.-% to about 0.8 wt.-% (calculation based on the ion of the element used).

The additives can be added to the zirconium oxide powder before conducting a pressing and/or pre-sintering step or can be added afterwards, e.g. after a pre-sintering step but before a final sintering step. The additives can be added either as a solid substance or applied to a pre-sintered article using a colouring solution or colouring composition, e.g. by dipping the article into a composition comprising the desired additive or by applying the composition comprising the desired additive on the surface of the article (e.g. by brushing or spraying). Such processes are described in more detail e.g. in U.S. Pat. No. 6,709,694 or EP 1 486 476 A1, wherein the disclosure of these documents is herewith incorporated by reference.

According to a particular embodiment the dental article comprises (in the sintered ceramic, all components are present as oxides):

$ZrO_2$: from about 80 wt.-% to about 99 wt.-% or from about 90 wt.-% to about 97 wt.-%, $Y_2O_3$: from about 0.5 wt.-% to about 10 wt.-% or from about 2.5 wt.-% to about 6 wt.-%, $Dy_2O_3$: from about 0.15 wt.-% to about 7.5 wt.-% or from about 0.75 wt.-% to about 3 wt.-%, $Nd_2O_3$: from about 0.014 wt.-% to about 1.4 wt.-% or from about 0.14 wt.-% to about 0.4 wt.-%, and Additives: from about 0.0001 wt.-% to about 1 wt.-% or from about 0.001 wt.-% to about 0.8 wt.-%, wherein the term additive includes components other than $ZrO_2$, $Y_2O_3$, $Dy_2O_3$ and $Nd_2O_3$.

A dental article having the above composition is especially suitable for producing a dental restoration or part thereof, especially a dental support structure. The final dental restoration or dental support structure has typically a white, slightly bluish colour or can take shades of yellow and brown if further colouring additives are applied and it mimicries the appearance of natural human or animal dentin.

In certain embodiments the dental article (before conducting a final sintering or firing step) can typically be characterized by at least one or more, sometimes all of the following features:

raw breaking resistance: from about 5 to about 55 MPa, or from about 5 to about 30 MPa, density: from about 2.8 to about 3.5 $g/cm^3$, or from about 2.9 to about 3.1 $g/cm^3$.

The raw breaking resistance can be determined according to DIN EN ISO 6872 (with the following modifications: diameter of steel ball: 6 mm; diameter of support circle: 14 mm; diameter of flat punch: 3.6 mm; diameter of sample disc: 20 mm, thickness of sample disc: 2 mm; no grinding and polishing of samples.).

In certain embodiments the dental article (after conducting a final sintering or firing step) fulfils at least one or more, sometimes all of the following features:

breaking resistance: at least about 400 MPa, or at least about 700 MPa or at least about 1000 MPa, density: from about 5.9 to about 6.1 $g/cm^3$ or from about 6.0 to about 6.1 $g/cm^3$, and/or light emission, in particular, fluorescence emission in the region of about 470 nm to about 510 nm.

The breaking resistance of the sintered dental ceramic article can be determined according to the "punch on three ball test" (biaxial flexural strength) described in DIN EN ISO 6872, edition March 1999, with the following modifications: diameter of steel ball: 3 mm; diameter of support circle: 12 mm; diameter of flat punch: 3.6 mm; diameter of sample disc: 16 mm, thickness of sample disc: 1.6 mm (+/−0.05 mm); grinding of samples with 10 μm disc to be +/−0.05 mm plan parallel and polishing of samples consecutively with 9 and 3 μm.

The density can be obtained from determining the mass (by weighing) and the volume (e.g. by calculation or using the "Archimedes Method").

The fluorescence spectrum can be obtained as described in detail in the experimental section below.

Typical firing or sintering temperatures include a range from about 1200° C. to about 1500° C.

A zirconium oxide containing green body can be produced by any standard procedure known to the person skilled in the art, including uniaxial pressing, cold isostatic pressing (CIP), and slip casting.

According to one embodiment, the colouring substance can be added before production of a green body by mixing a zirconium oxide containing material with substance A and/or substance B.

Adding the substances from the very beginning, i.e. before the zirconium oxide containing material is pressed into a certain shape, often results in a very homogeneous distribution of the substances throughout the powder mixture.

According to another embodiment, the substance can be added after a pre-sintering step of a zirconium oxide containing material e.g. by infiltrating the zirconium oxide containing material with a composition containing the desired ions.

Using the infiltration route can facilitate the whole production process e.g. by reducing the number of process steps needed for providing a coloured and fluorescent material.

Another embodiment of the invention is directed to the production of dental mill blocks comprising a dental article having fluorescent properties. The dental mill blank can be used for producing a dental support structure.

Thus, the inventive dental article can be produced using different methods.

Thus, one embodiment (Option A) is directed to a process comprising the steps of
a) providing a composition comprising zirconium oxide powder, a liquid, substance A and substance B,
b) casting the composition in a mould to obtain a green body,
c) optionally pre-sintering the green body to obtain a pre-sintered article
d) optionally machining the green body obtained in step b) or the pre-sintered article obtained in step c), and
e) optionally firing the article from step b), step c) or step d).

Liquids which can be used include water and low boiling alcohols (e.g. methanol, ethanol, and propanol) and ketons (e.g. acetone).

This process is exemplified in FIG. 1a. FIG. 1a is a flow chart showing a production route using a slip casting method.

Pre-sintering, if desired, can be carried out in a temperature range from about 700° C. to about 1000° C. or from about 800° C. to about 950° C.

Another embodiment (Option B) is directed to a process comprising the steps of
a) providing a composition comprising zirconium oxide, substance A and substance B,
b) applying pressure and/or temperature to the composition to obtain a 3-dim article,
c) optionally machining the 3-dim article, and
d) optionally firing the 3-dim article.

Figure 1B:
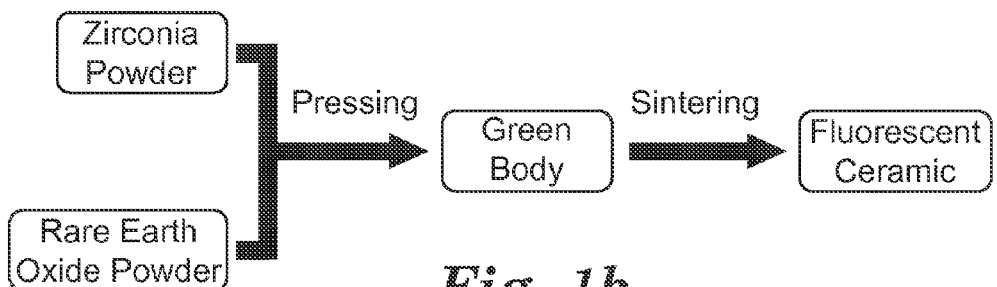

This process is exemplified in FIG. 1b. FIG. 1b shows a flow chart of possible production route comprising a pressing step.

Still another embodiment (Option C) is directed to a process comprising the steps of
a) providing a composition comprising zirconium oxide and substance A or substance B,
b) applying pressure and/or temperature to the composition to obtain a 3-dim article,
c) optionally machining the 3-dim article,
d) applying a composition containing a substance, which has not been used in step a), the substance being selected from substance B or substance A, to the article obtained in step b) or step c), and
e) optionally firing the article from step d).

Yet another embodiment (Option D) is directed to a process comprising the steps of
a) providing an article, especially a dental article, comprising zirconium oxide,
b) optionally machining the article of step a),
c) applying a composition comprising substance A and substance B to the article, and
d) optionally firing the article.

Figure 1C:
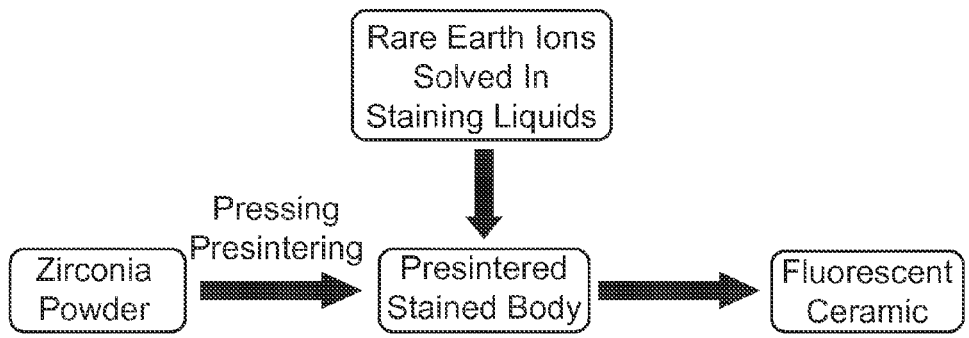

This process is exemplified in FIG. 1c. FIG. 1c shows a flow chart of a production route comprising a pressing and infiltration step.

The composition containing either substance A or substance B or substance A and substance B which is used in the processes above (Option C and Option D) is typically in a liquid stage. Thus, the composition typically contains a liquid or solvent in addition.

The composition should have an adequate viscosity so that sufficient wetting and colouring of and penetration into the pores of the zirconium oxide containing article can be achieved. Good results can be obtained with a solution having a dynamic viscosity of about 1 mPa*s up to about 100 mPa*s or up to about 80 mPa*s or up to about 60 mPa*s.

The dynamic viscosity can be determined with a Physica MCR301 instrument using a cone plate geometry, diameter 50 mm, angle (cone) 1°, at 23° C. A typical shear rate is 200 rounds/sec, however, generally the viscosity of liquids is independent from the shear rate in a wide range.

If the viscosity of the composition to be applied in this process is too low, the colour of the coloured dental article might not be homogenous.

Colouring the dental article is usually achieved by dipping the article into the composition. However, the composition can also be applied to the article by spraying, brushing, painting or by using a sponge or fabric.

The dental article is usually treated with the composition for about 1 to about 5 min, preferably from about 2 to about 3 min at room temperature (about 23° C.). Preferably no pressure is used.

Drying the coloured dental ceramic article is not absolutely necessary, but can be preferred to reduce the time needed for firing and to avoid undesired inhomogenous colour effects. Drying can be effected by simply storing the dental ceramic article on a surface at ambient conditions for a couple of hours (about 1 to about 3 h).

A typical composition which can be used in one of the process described above (especially Option C and Option D) comprises
a solvent in an amount of about 20 to about 99 or in an amount of about 55 to about 95 or in an amount of about 69 to about 90 wt.-%, optionally a soluble form of substance A in an amount of about 1 wt.-% to about 50 wt.-%, or in an amount of about 3 wt.-% to about 30 wt.-% or in an amount of about 7 wt.-% to about 20 wt.-%, optionally a soluble form of substance B in an amount of about 0.1 wt.-% to about 20 wt.-% or in an amount of about 0.7 wt.-% to about 7 wt.-% or in an amount of about 1 wt.-% to about 5 wt.-%, and optionally additives (like e.g. further colouring additives, stabilizers, temporary binders, buffers and/or thixotropic substances) in an amount of about 0.1 wt.-% to about 10 wt.-% or in an amount of about 1 wt.-% to about 8 wt.-% or in an amount of about 2 wt.-% to about 6 wt.-%, wt.-% with respect to the weight of the whole composition (including the solvent(s)), wherein the composition comprises either substance A or substance B or substance A and substance B.

Thus, according to a further embodiment the invention also relates to a composition as described above used for producing a dental article containing substance A and/or substance B, wherein substance A and substance B are as described in the text of the invention.

According to a preferred embodiment, the 3-dim article or the green body mentioned in the processes described above has the shape of a dental mill blank.

The dental article can also be sintered, if desired. Sintering conditions are dependant on the material used. An oven which can be used is the commercially available LAVA™ Therm (3M ESPE; Germany). During the sintering process the coloured dental ceramic article is sintered to its final shape, thereby undergoing changes with regard to dimension, density, hardness, raw breaking resistance and/or grain size.

The sintering usually takes place for a $ZrO_2$ based ceramic at a temperature above about 1300° C., preferably above about 1400° C., more preferably above about 1450° C. and lasts for at least about 0.5 h, preferably for at least about 1 h, more preferably for at least about 2 h.

Generally, the sintering conditions are adjusted such that the sintered dental article has a density of equal or greater than about 98% compared with the theoretically achievable density. In one embodiment this can be accomplished using a temperature above about 1300° C.

A further aspect of the invention relates to the use of the dental article described in the text of the invention for producing a dental restoration, including crowns, bridges, abutments and parts thereof. The crowns, bridges, abutments and parts thereof typically contain a support structure comprising the inventive dental article and a veneering structure or layer of a different material, e.g. a glass or glass ceramic material.

The production step typically includes the step of machining the dental article.

The inventive dental article is typically contained in a holding device like a frame or fixed on a stub. Holding devices including frames have been proven to be useful, if the dental article should be put in a magazine, either for storing or for machining. The holding device typically facilitates the machining of the dental article, e.g. by a machining device such as a milling device. Examples of holding devices are shown in US 2003/0132539, U.S. Pat. No. 6,769,912, and EP 0 455 854 B1 the content of which with regard to holding devices (e.g. frames and stubs or supporting body) is herewith incorporated by reference and regarded part of the text of the present invention.

Fixing of the dental article on a stub can be achieved e.g. by gluing. The fixing should be such that the dental article can be processed in a milling machine e.g. on a Cerec™ InLab machine available from Sirona AG, Bensheim, Germany.

According to one embodiment of the invention, the dental article comprises a dental support structure, the dental support structure comprising $ZrO_2$, substance A and substance B, wherein substance A and substance B are defined as described in the text of the invention.

According to another embodiment of the invention, the dental article comprises a dental support structure and a composition applied on the surface of the dental support structure, wherein the dental support structure comprises $ZrO_2$ and substance A and the composition comprises substance B, wherein substance A and substance B are defined as described in the text of the invention.

According to one embodiment the composition (containing substance B) to be applied on the dental support structure may migrate or diffuse into the pores of the support structure. This is typically the case, if a low viscous composition is used and/or substance B is contained in the composition in a soluble form (e.g. salt dissolved in a liquid).

According to another embodiment the composition (containing substance B) to be applied on the dental support structure may remain on the surface of the support structure. This is typically the case, if a high viscous composition is used or if substance B is contained in the composition in a non soluble form (e.g. as oxide).

The invention also relates to the use of either a composition containing substance A or a composition containing substance B for producing a dental article containing $ZrO_2$, wherein the dental article obtained after the production process comprises substance A and substance B.

The dental article of the present invention does typically not contain components or additives which jeopardize the intended purpose to be achieved with the present invention, i.e. providing an aesthetic dental restoration. Thus, components or additives added in an amount which finally results in a non-tooth-coloured article are usually not contained in the dental article. Typically, an article is characterized as not being tooth coloured if it cannot be allocated a colour from the Vita colour code system, known to the person skilled in the art. Additionally, components which reduce the mechanical strength of the dental restoration to a degree, where mechanical failure may occur, are also not included in the dental article.

Thus, the inventive dental article does typically not contain or is essentially free of either or more or all of the elements or ions of vanadium (V), chromium (Cr), cobalt (Co), nickel (Ni), copper (Cu) and/or silicon (Si).

According to another embodiment, the inventive dental article does typically not contain glass or glass ceramic material in an amount above about 10 or above about 5 or above about 2 wt.-% or is essentially free of glass or glass ceramic material, wt.-% with respect to the weight of the dental ceramic article.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements

Light Emission (Fluorescence)

The fluorescence properties were determined using an optical setup comprising the following parts: GC America G-Light as light source, irradiating light of around 409 nm wavelength, an Ulbricht sphere, fiber optics from Topsensor Systems as light conductor and an A/D converter. A sample having the shape of a disc (diameter of 16 mm, thickness of 1.6 mm) was used to cover the opening of the Ulbricht sphere. The light emission spectrum of the sample was measured while transilluminating it with excitation radiation (violet light).

Light Absorption

The light absorption properties were determined using an optical setup with the following parts: HL-200 from Micropack as light source, irradiating white light, an Ulbricht sphere, fiber optics from Topsensor Systems as light conductor and an A/D converter. A sample having the shape of a disc (diameter of 16 mm, thickness of 1.6 mm) was used to cover the opening of the Ulbricht sphere. The light transmission spectrum of the sample was measured while transilluminating it with white light.

The materials used for preparing the samples are listed in Table 2.

TABLE 2

| Name | Description | Availability |
| --- | --- | --- |
| Dolapix CE 64 | Auxiliary agent for slip preparation of ceramic powders | Zschimmer & Schwarz |
| TZ-3Y-E | Yttrium stabilized zirconia containing 0.25 wt.-% alumina. | Tosoh Corp. |
| TZ-3Y-SBE | Yttrium stabilized zirconia containing 0.25 wt.-% alumina. | Tosoh Corp. |
| TZ-3Y-SBC | Yttrium stabilized zirconia containing 0.25 wt.-% alumina. | Tosoh Corp. |
| LAVA ™ Frame Shade Dyeing Liquid FS 1 | containing small amounts of Pr, Er and Mn | 3M ESPE; Germany |

The rare earth element containing compounds can be obtained e.g. from Aldrich, Merck or Fluka, Germany. According to the information provided by the manufacturer, TZ-3Y-SBC and TZ-3Y-SBE powders contain binder material in two different amounts, whereas TZ-3Y-E powder is essentially free of a binder material.

Example 0

Figure 2A:
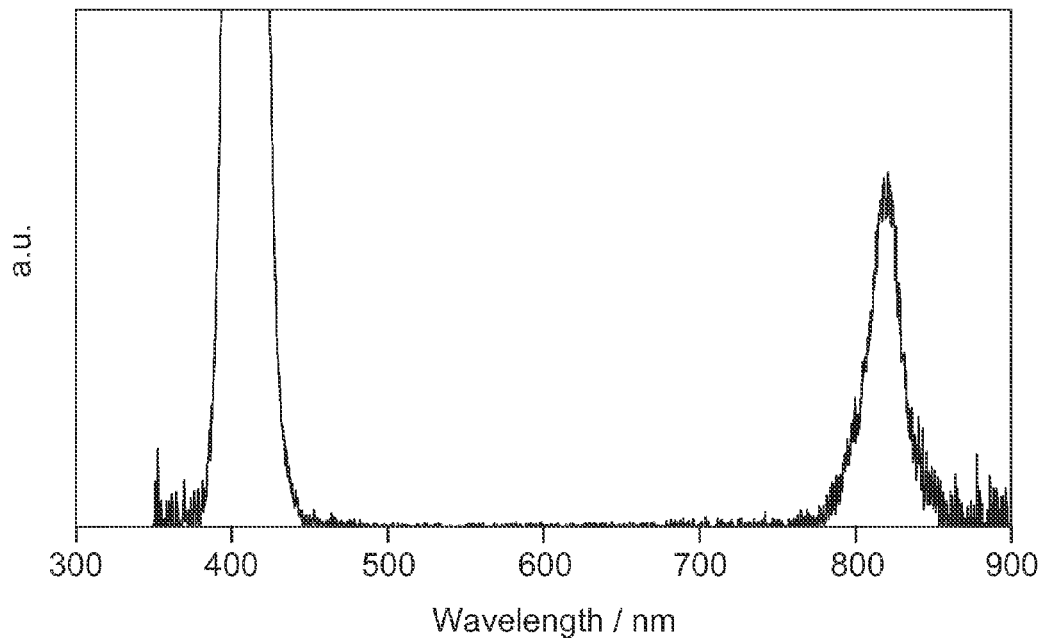
FIG. 2 *a* shows the spectrum of the excitation radiation with no sample in the light path.
Figure 2B:
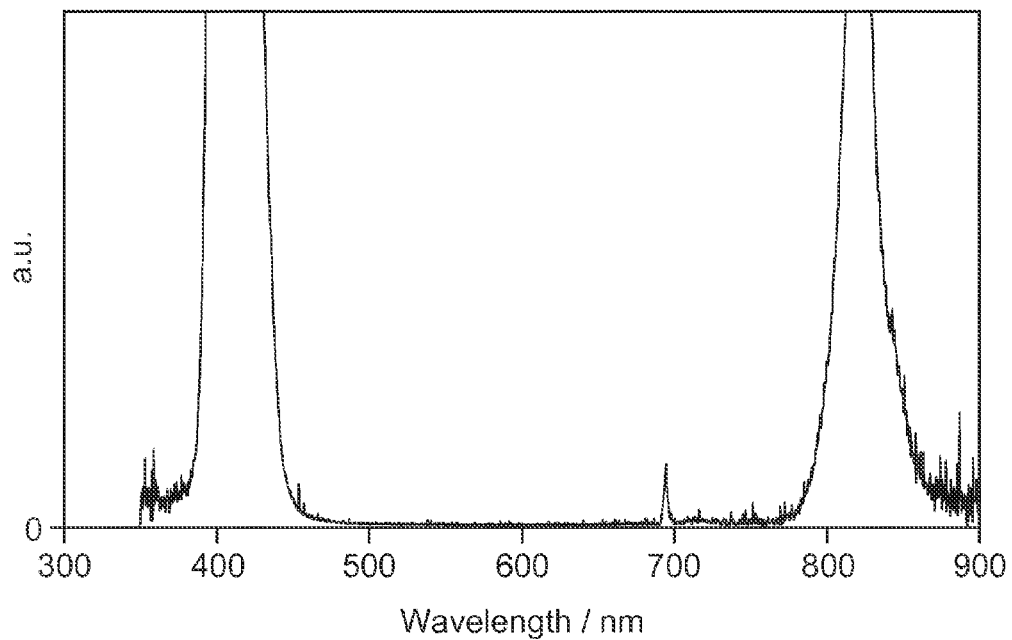

Zirconia green bodies were produced by pressing 2.1 g of TZ-3Y-SBC powder at a pressure of 6.4 tons. The green bodies were presintered at 800° C. The obtained discs were then fired in a LAVA™ Therm oven (3M ESPE) up to a temperature of 1500° C. The final ceramic was taken from the oven after reaching room temperature again. FIG. 2b shows the fluorescence spectrum of a sample containing no colouring additives.

Example 1

Figure 2C:
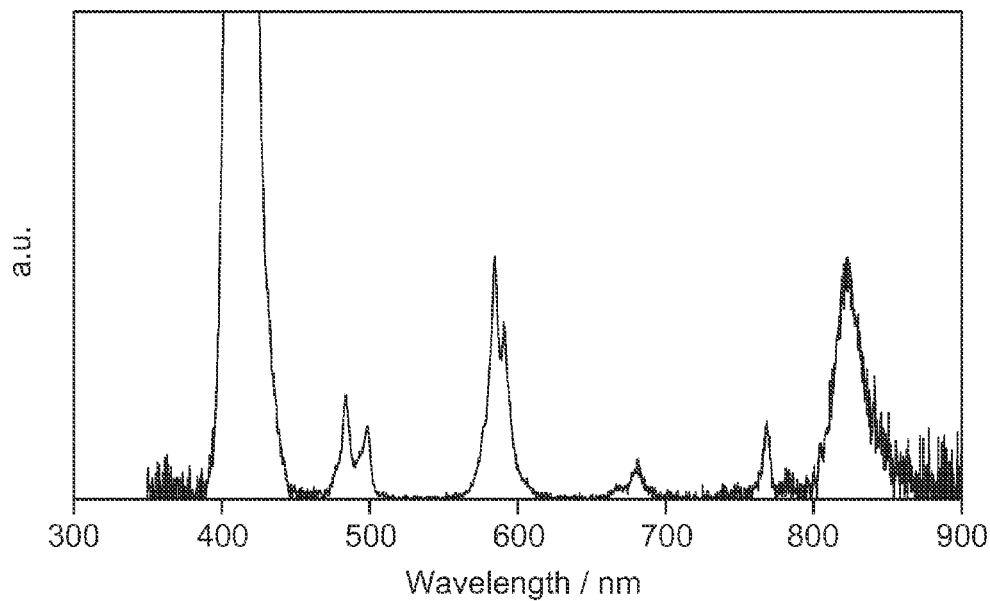

10.0 ml of de-ionized water and 0.25 ml of Dolapix™ CE 64 were placed in a beaker and mixed with a magnetic stirrer. 0.4 g of dysprosium oxide was dispersed in the solution. After that, the slip was produced by adding 39.0 g of zirconia powder TZ-3Y-E. The slip was cast into a mould of cylindric shape and a diameter of 20 mm made of silicone rubber and left to dry at ambient conditions. The green body was fired in a LAVA™ Therm oven up to a temperature of about 1500° C. without any extra calcination step. The final sintered ceramic was taken from the oven after reaching room temperature again. The sample fluoresced with slight yellow colour under violet light excitation (FIG. 2c).

Example 2

Figure 2D:
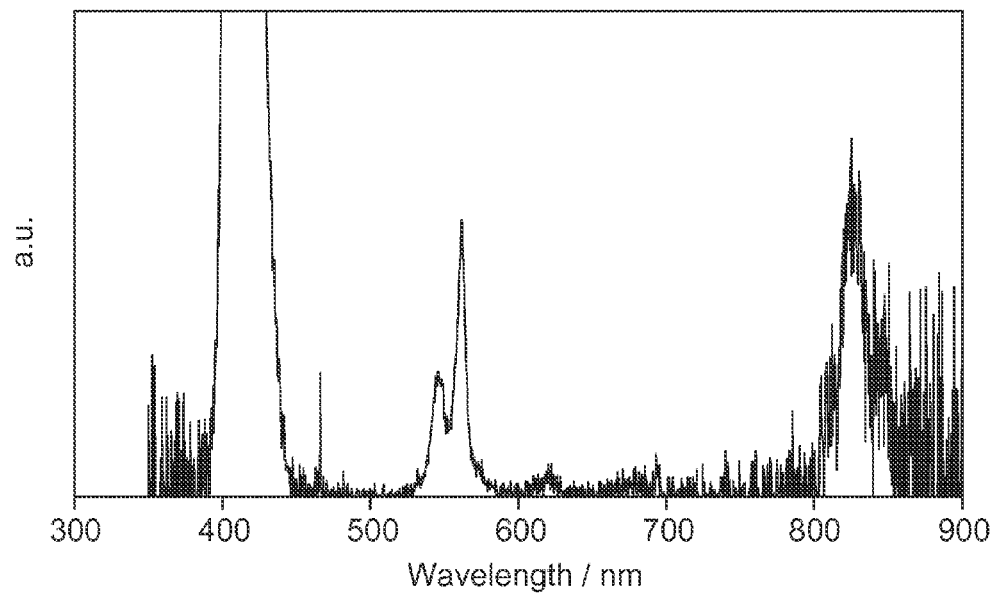

The process described in Example 1 was repeated except for using 0.4 g of erbium carbonate as fluorescent additive. The sample fluoresced with green colour under violet light excitation (FIG. 2d).

Example 3

Figure 2E:
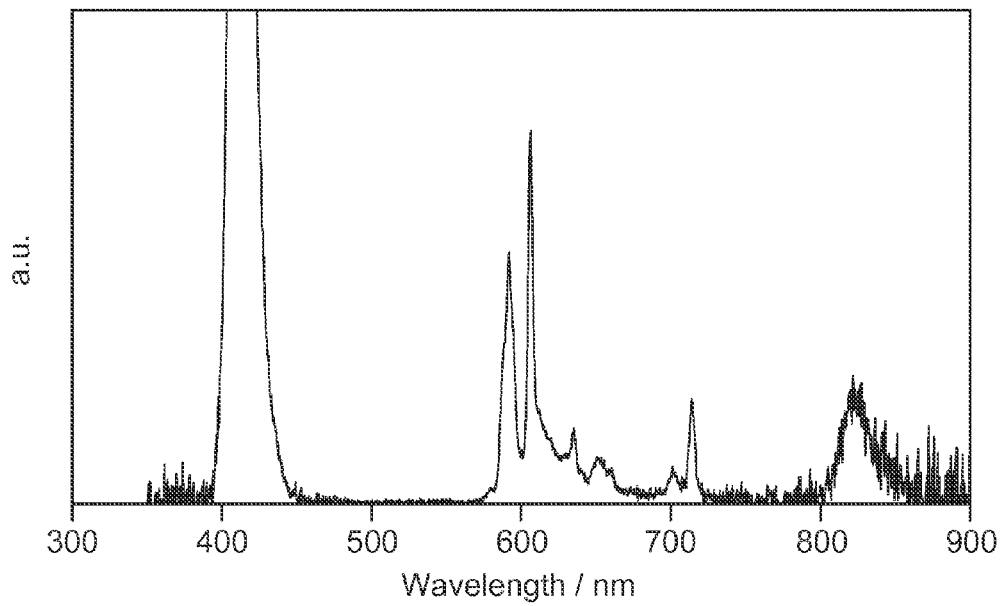

The process described in Example 1 was repeated except for using 0.4 g of europium oxide as fluorescent additive. The sample fluoresces with red colour under violet light excitation (FIG. 2e).

Example 4

Figure 2F:
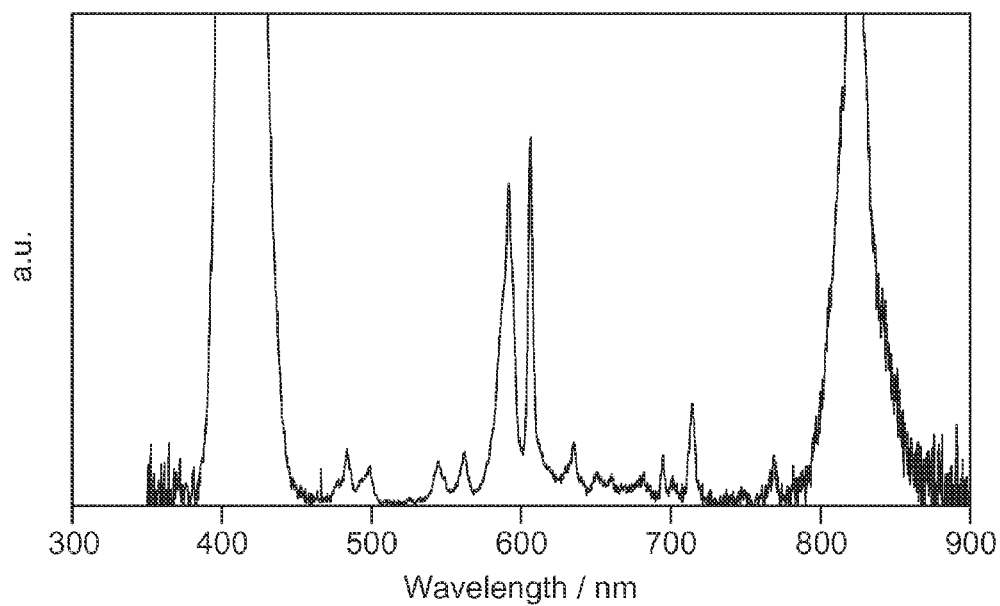

The process described in Example 1 was repeated except for using 0.2 g of each dysprosium oxide, erbium carbonate and europium oxide as fluorescent additive to yield a fluorescence colour different from each of the single additives. The sample fluoresces with bright yellow, almost white colour under violet light excitation (FIG. 2f).

Example 5

Zirconia green bodies were produced by pressing 2.1 g of TZ-3Y-SBE powder at a pressure of 6.4 tons. The green bodies were presintered at 800° C. The staining solution was made by adding 0.3 g of samarium acetate to 2.5 ml of LAVA™ Frame Shade Dyeing Liquid FS 1 (commercially available from 3M ESPE, Germany; lot number: 249730). The pre-sintered disc was put into the staining liquid for 5 min. Afterwards it was removed from the solution, wiped clean with a soft, wet cloth and dried at ambient conditions. The stained body was fired in a LAVA™ Therm oven up to a temperature of 1500° C. without any extra calcination step. The final ceramic was taken from the oven after reaching room temperature again. The sample fluoresces weakly with orange colour under violet light excitation (FIG. 3b).

Figure 3A:
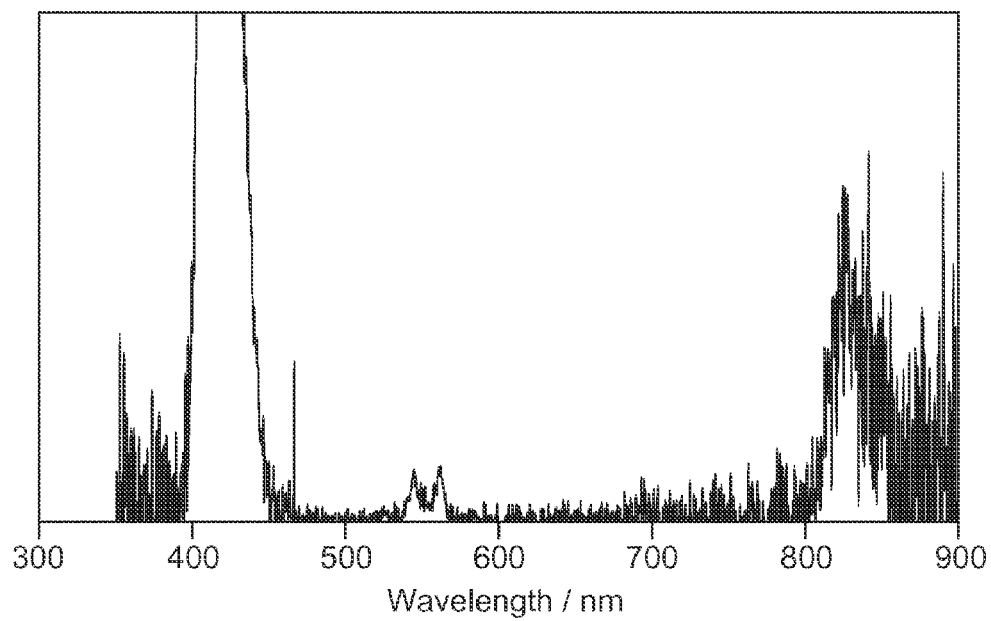
FIG. 3a shows the fluorescence spectrum of a sample coloured with a commercially available dyeing liquid containing erbium.
Figure 3B:
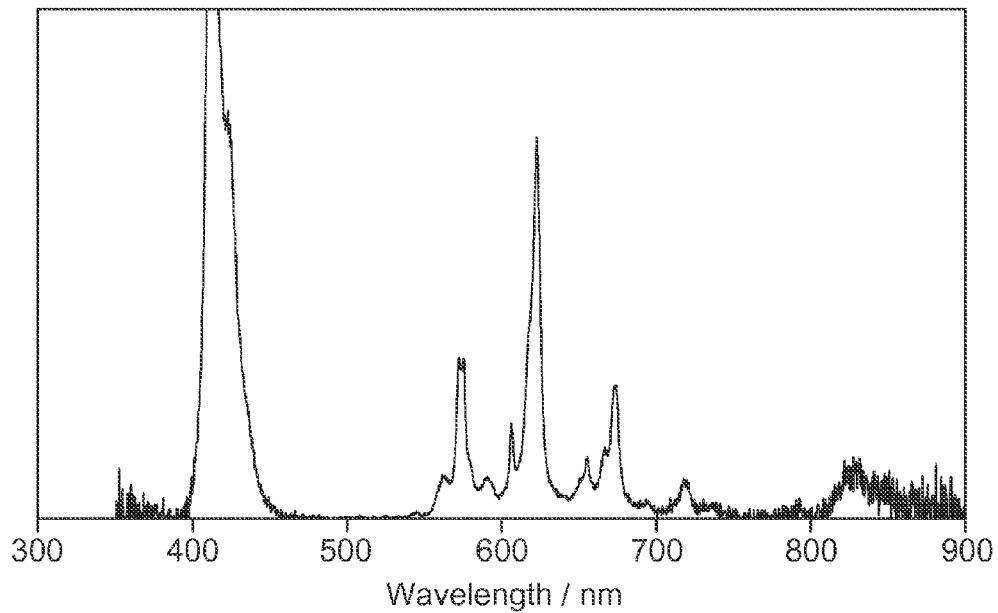
FIG. 3b shows the fluorescence spectrum of a sample coloured with a colouring liquid containing samarium.

The fluorescence spectrum of a sample coloured with LAVA™ Frame Shade Dyeing Liquid FS 1 containing a small amount of erbium is shown in FIG. 3a.

Example 6

Zirconia green bodies were produced by pressing 2.1 g of TZ-3Y-SBC powder mixed with 0.22 g of dysprosium oxide at a pressure of 6.4 tons into discs of 20 mm diameter and 2 mm thickness. The green bodies were pre-sintered at 800° C. The colouring solution was made by adding 0.05 g of neodymium acetate to 2.5 ml of de-ionized water. The pre-sintered disc was put into the colouring solution for 5 min. Afterwards it was removed from the solution, wiped clean with a soft, wet cloth and dried at ambient conditions. The stained body was fired in a LAVA™ Therm oven up to a temperature of 1500° C. without any extra calcination step. The final ceramic was taken from the oven after reaching room temperature again. The sample fluoresced with a more bluish colour than a sample containing dysprosium only.

Figure 4A:
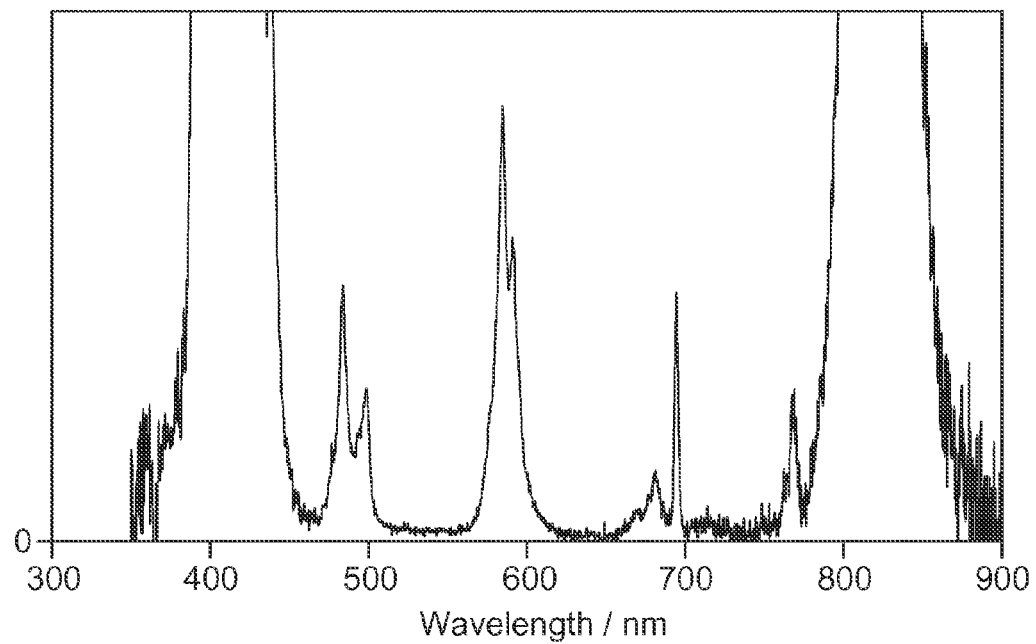
FIG. 4a shows the fluorescence spectrum of a sample containing dysprosium.
Figure 4B:
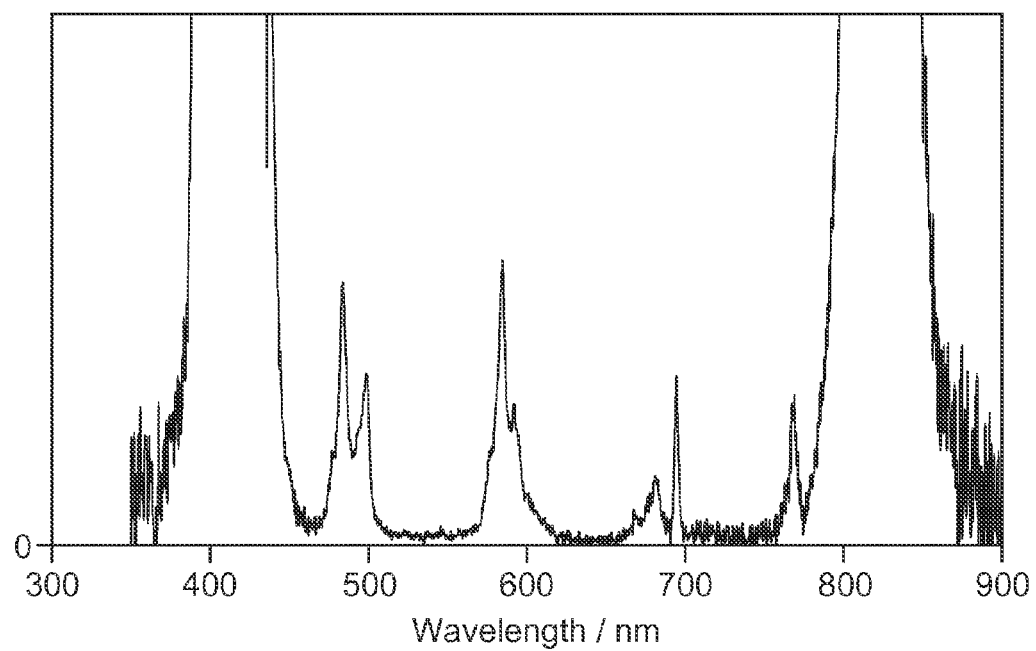
FIG. 4b shows the fluorescence spectrum of a sample containing dysprosium and neodymium.

The fluorescence spectrum of the sample containing dysprosium oxide only is shown in FIG. 4a. The spectrum of the sample with dysprosium oxide and neodymium acetate infiltrated is shown in FIG. 4b. The yellow band around about 580 nm is weakened compared to the other bands (e.g. blue at 480 nm) due to the addition of traces of neodymium. This may help in improving the aesthetic properties of the sample.

In FIG. 5a the light transmission spectrum of a 3Y-TZP zirconium oxide sample without any colouring additive is shown (range: 500 to 850 nm).

In FIG. 5b the light transmission spectrum of a 3Y-TZP zirconium oxide sample containing dysprosium is shown (range: 500 to 850 nm).

In FIG. 5c the light transmission spectrum of a 3Y-TZP zirconium oxide sample containing neodymium is shown (range: 500 to 850 nm).

Example 7

Zirconia green bodies were produced as described in Example 6, however, using 2.1 g TZ-3Y-SBC powder from TOSOH mixed with 0.44 g dysprosium oxide and pre-sintering at 900° C. All other compositions and working steps from Example 6 remain unchanged.

The invention claimed is:

1. A dental ceramic article comprising,
a dental support structure, wherein the dental support structure comprises zirconium oxide and at least two different coloring substances A and B, substance A showing a light emission in the range from about 470 nm to about 510 nm and substance B showing a light absorption in the range from about 520 nm to about 750 nm, wherein the dental support structure does not comprise a glass or glass ceramic material in an amount above about 10 wt.-% and wherein substance A is from about 3 wt.-% to about 7.5 wt.-%.

2. The dental ceramic article according to claim 1, substance A being selected from components comprising dysprosium.

3. The dental ceramic article according to claim 1, substance B being selected from components comprising neodymium.

4. The dental ceramic article according to claim 1, substance A being present in an amount in the range of about 0.1 to about 5 mol-% and substance B being present in an amount in the range of about 0.01 to about 1 mol-%, wherein the amounts of the substances are calculated as molar amounts of the cations.

5. The dental ceramic article according to claim 1 being characterized by at least one of the following features:
breaking resistance: at least about 400 MPa,
density: from about 5.9 to about 6.1 g/cm$^3$, and
light emission in the region of about 470 nm to about 510 nm.

6. The dental ceramic article according to claim 1 comprising:
$ZrO_2$: from about 80 wt.-% to about 99 wt.-%,
$Y_2O_3$: from about 0.5 wt.-% to about 10 wt.-%,
$Dy_2O_3$: from about 2 wt.-% to about 7.5 wt.-%,
$Nd_2O_3$: from about 0.014 wt.-% to about 1.4 wt.-%, and
Additives: from about 0.0001 wt.-% to about 1 wt.-%.

7. The dental ceramic article according to claim 1 fixed in or to a holding device.

8. A process of producing the dental ceramic article according to claim 1, the process comprising the steps of
a) providing a composition comprising zirconium oxide, a liquid, substance A, substance B and optionally a binder,
b) casting the composition in a mould to obtain a 3-dimensional article,
c) pre-sintering the 3-dimensional article to obtain a pre-sintered article,
d) machining the 3-dimensional article obtained in step b) or the pre-sintered article obtained in step c), and firing the article from step b), step c) or step d).

9. A process of producing the dental ceramic article according to claim 1, the process comprising the steps of
a) providing a composition comprising zirconium oxide, substance A and substance B,
b) applying pressure and/or temperature to the composition to obtain a 3-dimensional article,
c) optionally machining the 3-dimensional article, and optionally firing the 3-dimensional article from step b) or step c).

10. A process of producing the dental ceramic article according to claim 1, the process comprising the steps of
a) providing a dental article comprising zirconium oxide,
b) optionally machining the dental article of step a),
c) applying a composition containing substance B and substance A to the dental article, and
d) optionally firing the dental article.

11. A process of producing the dental ceramic article according to claim 1, the process comprising the steps of
a) providing a composition comprising zirconium oxide and substance A or substance B,
b) applying pressure and/or temperature to the composition to obtain a 3-dimensional article,
c) optionally machining the 3-dimensional article,
d) applying a composition containing a substance which has not been used in step a), the substance being selected from substance B or substance A, to the article obtained in step b) or step c), and
e) optionally firing the article from step d).

12. A method of producing a dental restoration or a part thereof, the method comprising
providing the dental ceramic article according to claim 1; and
machining the dental ceramic article.

13. A process for producing a dental ceramic article as described in claim 1, the process comprising applying to the dental ceramic article a composition comprising
a solvent in an amount of about 20 to about 99 wt.-%,
substance A and substance B, and
optionally additives in an amount of about 0.1 wt.-% to about 10 wt.-%,
wherein substance A is present in an amount of about 3 wt.-% to about 7.5 wt.-%, and substance B is present in an amount of about 0.1 wt.-% to about 20 wt.-%, wt.-% with respect to the weight of the whole composition.

* * * * *

UNITED STATES PATENT AND TRADEMARK OFFICE
CERTIFICATE OF CORRECTION

| | | |
|---|---|---|
| PATENT NO. | : 8,841,223 B2 | Page 1 of 1 |
| APPLICATION NO. | : 13/131428 | |
| DATED | : September 23, 2014 | |
| INVENTOR(S) | : Michael Jahns | |

It is certified that error appears in the above-identified patent and that said Letters Patent is hereby corrected as shown below:

<u>Title Page, Column 2, References Cited (Other Publications)</u>
Line 8                    Delete "Nanycrystalline" and insert -- Nanocrystalline --, therefor.

<u>In the Specification</u>
<u>Column 3</u>
Line 29 (Approx.)         Delete "extend" and insert -- extent --, therefor.

Signed and Sealed this
Thirty-first Day of March, 2015

Michelle K. Lee
*Director of the United States Patent and Trademark Office*